United States Patent [19]

Mehl

[11] 4,369,038

[45] Jan. 18, 1983

[54] TRANSFER-PRINTING PAPER, ITS MANUFACTURE AND USES

[75] Inventor: Wolfgang Mehl, Geneva, Switzerland

[73] Assignee: Ciba-Geigy Ltd., Basel, Switzerland

[21] Appl. No.: 128,420

[22] Filed: Mar. 10, 1980

[30] Foreign Application Priority Data

Mar. 12, 1979 [CH] Switzerland .......................... 2316/79
Aug. 9, 1979 [CH] Switzerland .......................... 7309/79

[51] Int. Cl.³ ............................................. B41M 3/12
[52] U.S. Cl. .............................................. 8/471; 8/532; 8/918; 8/924; 8/927; 106/22; 427/148
[58] Field of Search ................... 8/471, 532; 427/148; 106/22

[56] References Cited

U.S. PATENT DOCUMENTS

| | | | |
|---|---|---|---|
| 4,083,205 | 4/1978 | Clarke et al. | 8/471 |
| 4,088,442 | 5/1978 | Hugelin et al. | 8/471 |
| 4,116,022 | 9/1978 | Lopata et al. | 8/471 |
| 4,119,397 | 10/1978 | Synder | 8/471 |
| 4,178,782 | 12/1979 | Schiffer | 8/471 |
| 4,207,069 | 6/1980 | Ono | 8/471 |
| 4,210,412 | 7/1980 | Yamane et al. | 8/471 |

FOREIGN PATENT DOCUMENTS

| | | |
|---|---|---|
| 1105734 | 3/1968 | United Kingdom . |
| 1189026 | 4/1970 | United Kingdom . |
| 1221126 | 2/1971 | United Kingdom . |
| 1423358 | 2/1976 | United Kingdom . |

OTHER PUBLICATIONS

Venkataraman, K., "The Chemistry of Synthetic Dyes," vol. VIII, Academic Press, 1978, pp. 202 and 213.

*Primary Examiner*—A. Lionel Clingman
*Attorney, Agent, or Firm*—Joseph G. Kolodny

[57] ABSTRACT

Auxiliary supports for dry transfer printing, which comprise dyestuffs of which the shades obtained by transfer at 205° C. do not reach 60% of the intensity obtained by transfer at 235° C.

15 Claims, No Drawings

TRANSFER-PRINTING PAPER, ITS MANUFACTURE AND USES

Transfer printing (also known under the name dry heat-printing or vapour phase heat-printing), the principle of which is described, for example, in French Pat. Nos. 1,223,330 and 1,585,119, uses auxiliary supports, generally made of paper, which carry one or more dyestuffs which, within a temperature range between 160° and 220° C., pass from the auxiliary support to the substrate to be printed. The dyestuffs of this type are from the class of the so-called disperse dyestuffs which, as is known, have no affinity, or too little affinity, for cellulose fibres, whereupon transfer printing has developed virtually only in the field of synthetic fibres and mainly in the field of woven and knitted polyester fabrics. Attempts have been made to overcome the disadvantages of this printing method in various ways, for example by using so-called "vacuum" calenders, which make it possible to accelerate the transfer process, or by using carbinol bases of cationic dyestuffs, which also make it possible to dye and print acrylic fibres, such as polyacrylonitrile, by this process, or also by pretreating the cellulose fibres (French Pat. No. 2,254,676) in order to impart thereto an adequate affinity for the dyestuffs used in transfer printing. Nevertheless, despite all these efforts, the dry transfer printing of textiles still suffers from many limitations, and, taking everything into account, the main limitations always arise from the low fastness obtainable with all the modifications of the process, and also from the limited number of types of auxiliary supports available.

The object of the present invention is to overcome, to a large extent, the diadvantages of the known auxiliary supports. It relates to new auxiliary supports and to inks suitable for printing them. It also relates to a heat-printing process using these new auxiliary supports; in particular, it relates to new auxiliary supports which enable a better fastness to be obtained by dry transfer onto polyester. Some of these new auxiliary supports even make it possible to print materials which could not be printed in fast shades with the known supports.

In general terms, the present invention considerably enlarges the field of application of the dry transfer printing process, especially in the field of reduced pressure transfer and in the field of its application to the printing of textiles containing cellulose fibres, for example cotton and polyester/cotton blends.

The auxiliary supports of the present invention are characterised in that they carry, on a heat-stable flexible base, preferably on one of the sides of a sheet or strip of paper, cellophane or aluminium, one or preferably several dyestuffs which, at 205° C. and at atmospheric pressure, transfer onto polyester (or onto cotton impregnated with polyethylene glycol) to give shades, the optical density of which does not reach 50%, and preferably not even 30%, of that obtained with the conventional dyestuffs, that is to say with the yellow dyestuff hydroxyquinophthalone, the red dyestuff 1-amino-2-phenoxy-4-hydroxyanthraquinone and the blue dyestuff 1-amino-2-cyano-4-anilinoanthraquinone, when this optical density is measured on a densitometer fitted with the corresponding filter.

The dyestuffs to be used for printing the auxiliary supports of the present invention are therefore dyestuffs which, when transferred in the course of 35 seconds onto polyester or onto cotton containing polyethylene glycol (at least 8%), only reach the maximum of their transfer curve above 230° C., whereas, in the known dry transfer processes in the vapour phase, the auxiliary supports used carry dyestuffs which reach their maximum colour yield by transfer at 205°–215° C. in the course of 25 to 40 seconds.

By heating at a higher temperature or for a longer time, their colour yield is only changed very slightly; for some dyestuffs, the intensity only increases to a negligible extent (this is the case of the so-called class D or even C dyestuffs), whereas for others, for example those of the so-called A and B classes, and for certain class C dyestuffs used in conventional transfer, the intensity of the shades obtained sometimes even decreases when transfer is carried out above 210°–215° C. or when the transfer time is increased.

The auxiliary supports of the present invention are characterised in that they carry one or more dyestuffs, the intensity of which, for transfer onto cotton swollen with 8 to 10% of polyethylene glycol, constantly increases, even above 230° C. At 205° C. and at atmospheric pressure, these dyestuffs transfer onto cotton impregnated with polyethylene glycol to give shades, the optical density of which, after a transfer time of 35 seconds, does not reach 60%, and preferably not even 50%, of that obtained with these same dyestuffs under the same transfer conditions, but at 235° C.

Under a pressure of 50 to 120 mbars and for transfers carried out at 235° C., the supports of the present invention give prints having an optical density which is entirely comparable to those obtained with the known transfer papers, under the conventional transfer conditions, that is to say at 205° C., at atmospheric pressure and using similar amounts of dyestuffs.

In the present case, the term optical density is understood as meaning the absolute value of the logarithm of the fraction of light reflected by the surface of the final support onto which the dyestuff or dyestuffs have transferred.

This optical density can be measured by any suitable means, for example on a densitometer fitted with the corresponding filter. Thus, on a Macbeth type RD 514 reflection densitometer, a very pale shade which reflects 60% of the incident light has an optical density of 0.22 (log 0.6 = −0.22), whilst a less pale shade which reflects, for example, 50% of the incident light has an optical density of 0.30 (log 0.5 = −0.30), and so on. The prints having deeper shades, which reflect, for example, the percentages of incident light indicated in the table below, have the optical densities shown opposite:

| % of incident light reflected by the print | optical density |
| --- | --- |
| 40 | 0.40 |
| 30 | 0.52 |
| 25 | 0.60 |
| 20 | 0.70 |
| 15 | 0.82 |
| 10 | 1.00 |
| 6 | 1.22 |
| 5 | 1.30 |
| 4 | 1.40 |
| 3 | 1.52 |
| 2 | 1.70 |
| 1.5 | 1.82 |
| 1 | 2.00 |

The term corresponding filter is understood as meaning a filter of the complementary colour, that is to say green in the case of red shades, blue in the case of yellow shades and orange-red in the case of blue shades. In the case of mixed, violet, green and orange shades, the measurements are carried out with one filter and then with the other and that which gives the highest values is arbitrarily chosen. It is also possible to use the neutral filter or to carry out the measurements on all the shades with each filter and only to single out those filters which give the highest values.

In this way, it is easy to determine which dyestuffs, amongst those which sublime below 320° C., can be used for preparing the auxiliary supports of the present invention.

To do this, it suffices to prepare a printing ink containing 5 or 10% of the dyestuff which it is desired to test; using this ink, a sheet of paper is printed with an engraved cylinder or with a bar fitted with a graduated spiral which makes it possible to deposit a known amount of ink per unit surface area; the printed paper is then dried and the ink is transferred, for 35 seconds at 205° C. and 35 seconds at 235° C., onto cotton containing 10% of a polyethylene glycol having a molecular weight of 400. The optical density is measured after each transfer. The dyestuffs giving prints of which the optical density, at 205° C., is less than 60% of that obtained at 235° C. are suitable dyestuffs for use in the preparation of the auxiliary supports of the present invention. These dyestuffs, in contrast to those used in the known processes, reach the maximum of their transfer curve above 230° C., in a transfer time of 35 seconds, when transferring onto cotton impregnated with at least 8% of a polyethylene glycol having a molecular weight of 300 or 400. They sublime or vaporise below 320° C., preferably even below 270° C., without substantial decomposition, and transfer at 235° C. from the auxiliary support onto the material to be printed, at a rate of at least 60% in less than 100 seconds. At 205° C. and at atmospheric pressure, they only give inadequate transfers, the optical density of which is between 0.15 and at most 0.75 when the dyestuffs are present in amounts of 0.6 to 1.2 g per m² in the coloured zone of the auxiliary support.

The chemical constitution of these dyestuffs can vary considerably from one to the other. In general terms, their molecule does not contain highly ionic groups such as sulphonic acid and carboxylic acid groups; it contains at least three hexa-atomic rings, for example three benzene nuclei or one benzene nucleus and one naphthalene or anthraquinone nucleus.

Very good results are obtained with the dyestuffs which contain a phenoxyacetic acid or phenoxy—CO—O—CH$_2$CH$_2$— substituent bonded either to a benzene radical of a monoazo or disazo dyestuff or to a monoanthraquinone radical, and in which the phenoxy group can carry substituents such as one or more methyl or methoxy radicals or a fluorine, chlorine or bromine atom. Other dyestuffs which can also be used to prepare the auxiliary supports according to the invention contain 4 to 5 hexa-atomic rings and at least one —CO— group (possibly enolised) and one —NH— group. These two groups can form part of one and the same ring, as in phthaloylacridone and its chlorinated derivatives, or aminophthaloylacridone; they can also form a —CONH— bond between two aromatic rings or between an aliphatic radical and a benzene ring of the dyestuff molecule. These dyestuffs can equally well be of the anthraquinone, azo or even indigo type, in particular of the thioindigo type.

For printing onto cotton or onto a fibre blend, mainly onto polyester/cotton, the supports of the present invention which carry one or more dyestuffs from the following classes have a very special value:

(a) halogenated, preferably chlorinated or brominated, diphenylaminoanthraquinones;

(b) alkylimides of 1,4-diaminoanthraquinone-2,3-dicarboxylic acid, in which the alkyl carries one or two phenyl radicals;

(c) 1-benzoylaminoanthraquinones which carry a phenyl—NH— radical in the 4-, 5- or 8-position;

(d) phenylamides of 1-phenylazo-2-hydroxy-3-naphthoic acid, preferably those which do not have nitrogen-containing substituents; and (e) phenylamides or naphthylamides of α-phenylazo-acetylacetic acids and α-phenylazo-benzoylacetic acids, in particular those which do not have nitrogen-containing substituents.

In all these classes of dyestuffs, the phenyl and benzoyl radicals can contain simple substituents, such as methyl, ethyl, chlorine, bromine, methoxy or trifluoromethyl groups, or even tert.-butyl or iso-amyl groups, but preferably do not have nitrogen-containing substituents.

The dyestuffs to be used for preparing the auxiliary supports of the present invention are generally known. Some are commercially available in the ranges produced by dyestuff manufacturers. Thus, for example, some are available in the so-called TERASIL series from Ciba-Geigy, in the so-called CELLESTREN series from BASF and in the so-called DYBLN series from Du Pont. Those which are not commercially available can easily be manufactured in accordance with methods which are in themselves known; such dyestuffs are described in German Patents and German Patent Applications Nos. 2,618,032, 2,700,223, 2,608,345, 2,634,427, 2,640,576, 2,654,434, 2,524,243, 2,528,793 and 1,811,796 and also in Swiss Pat. No. 599,287 and U.S. Pat. Nos. 3,752,645, 3,835,154 and 3,888,624.

The following may be mentioned as characteristic examples of dyestuffs which can be used: the pink dyestuff DYBLN B, the yellow dyestuffs TERASIL-X 3G, CELLESTREN 5G and DYBLN G, the blue dyestuffs DYBLN R and 2R and CELLESTREN B, the brilliant blue dyestuffs TERASIL-X 2G and DYBLN GN, the scarlet dyestuff DYBLN G, the violet dyestuffs DYBLN R and CELLESTREN B, the red dyestuff DYBLN BBR and the pink dyestuff TERASIL-X 3GL, the blue-green dyestuff DYBLN 2G, 1-amino-2-methoxy-4-toluenesulphonyl-aminoanthraquinone, 1,4- and 1,5di-butyrylamino-anthraquinone and also the corresponding derivatives of methoxy-benzoic acid and trifluoromethylbenzoic acid, benzoylamino-iso-thiazolanthrone, the phenylamides of the 1-phenylazo-2-hydroxy-3-napthoic acids which carry, on one or other or on both of the phenyl radicals, one or more substituents chosen from the group comprising halogen atoms, in particular fluorine, chlorine and bromine, and methyl, ethyl, isopropyl, methoxy, ethoxy, trifluoromethyl and acetyl radicals, 1-benzoylamino-4-anilinoanthraquinone, 1-phenylbenzoylamino-anthraquinone, 1-phenylazobenzoylamino-anthraquin-one, 1-phenylbenzoylamino-4-methoxyanthraquinone, 1-benzoylamino-4-(p-isopropyl or isoamylanilino)-anthraquinone, the monoazo dyestuffs obtained by coupling the naphthanilide of acetylacetic or benzoylacetic acid with nitraniline or diazotised nitrotoluidine, the product obtained by coupling barbituric acid with diazotised nitroanisidine, the products obtained by coupling the diazo derivative of nitro-phenylaniline with the naphthanilide of acetylacetic or benzoylacetic acid, and the dioxazines obtained by cyclising the products resulting from the condensation of chloranil (tetrachloro-p-benzoquinone) with naphthylamine, aminopyrene, aniline and its derivatives such as p-chloroaniline, toluidine, anisidine, cresidine, p-isopropylaniline, m-trifluoromethylaniline and p-dimethylamino-aniline.

The preparation of the supports of the present invention, with these dyestuffs, is carried out in accordance with the customary processes, for example in accordance with the processes described in French Pat. Nos. 1,223,330 and 1,575,069, that is to say that inks containing the indicated dyestuffs are prepared. These inks can be of the offset type, water-based inks or solvent-based inks, all these techniques being well known to ink manufacturers. For example, it is possible to use water-miscible or water-immiscible solvents, or mixtures thereof, having a boiling point, at atmospheric pressure, which is below 120° C. and preferably below 105° C. Examples of such solvents which may be mentioned are halogenated or non-halogenated hydrocarbons of the aliphatic or aromatic series, such as toluene, cyclohexane and petroleum ether, low molecular weight alcohols, such as methanol, ethyl alcohol, propyl alcohol and isopropyl alcohol, esters of aliphatic acids, such as ethyl acetate, ketones, such as methyl ethyl ketone, and the like.

In addition to the dyestuff and the solvent, the inks also contain a heat-stable thickener or binder, that is to say a thickener or binder which does not decompose at the temperature at which the transfer according to the present invention is carried out. The thickeners or binders must be capable of drying to give, on the support, a non-adhesive layer which retains the dyestuff or dyestuffs used, without modifying them. Examples which may be mentioned are those which are capable of being dried, for example in a stream of hot air, so as to form a non-adhesive layer on the sheet of the printed support, such as, for example, polysaccharide ethers or esters and nitrocelluloses, in the case of solvent-based inks. As particularly suitable binders for solvent-based inks, there may be mentioned cellulose esters, for example cellulose acetobutyrate, and in particular cellulose ethers, such as ethyl-, propyl- and benzyl-cellulose and also mixtures thereof, and very particularly hydroxypropylcellulose and mixtures of cellulose ethers containing hydroxypropylcellulose. The binders for water-based inks are well known. As regards offset inks, drying oil acts both as the solvent and the binder.

All or part of a support is printed with the inks prepared in this way. The printing can be carried out on the machines usually employed for this kind of work, or on machines which have one or more additional rollers in front of or behind the actual inking rollers.

The supports obtained make it possible, depending on the dyestuffs used, to dye or print synthetic or natural materials. This dyeing or printing, which also forms the subject of the present invention, consists in bringing the temporary support, which has been printed, at least in part, in the manner described, into contact with material to be transfer-printed, which is preferably heated, during this bringing into contact, at a temperature of the same order of magnitude as that at which the dyestuffs change into the vapor phase, so that the latter do not simply condense on the surface of the material. The dyeing or printing thus amounts to one pass on a plate or on a heat calander or on any other apparatus which makes it possible to bring the temporary support contact with the material to be dyed, and to keep them at the requisite temperature, for the necessary time and under a pressure of 30 to 120 mbar, preferably under a pressure of 70 to 120 mbar.

When printing synthetic materials, no subsequent washing or vaporisation treatment is necessary in order to ensure the fixing of the dyestuff or to avoid its subsequent bleeding. In case of materials of natural origine, such as cotton and regenerated cellulose, it is indispensable that they are impregnated before transfer-printing with a dyestuff acceptor which is generally also a swelling agent for cellulose. Such an agent may be a polyol, diethylene glycol, polyethylene glycol, polypropylene glycol or esters such as a boric acid esters of polyols. After transfer printing it is generally necessary to remove the acceptor, for example by rinsing or by steam distillation, and this also makes it possible to fix the dyestuff to the fibre; if desired, the fibre can then be subjected to any desired finishing treatments (to render it crease-resistant, non flammable or the like).

The new supports of the present invention are suitable for the heat-printing of the most diverse synthetic materials, namely superpolyamides (polymers of $\epsilon$-caprolactam or of hexamethylenediamine adipate), polyesters, in particular linear polyesters such as polyethylene terephthalate, polyacrylonitrile and the like. The materials to be heat-printed can be presented in the most varied forms, for example in the form of sheets, films, felts, layers, and coatings for fibres, for example textile fibres in the form of flock, yarns, velvets, carpets, knitted fabrics, canvasses or woven fabrics of varying thickness, in the pure form or blended, for example, with cotton or wool. The supports permit a greater flexibility in application, they frequently permit a better yield and, in particular, they can be used for the heat-printing of materials which could not be printed by transfer, to give an adequate fastness, using the known auxiliary supports.

In the non-limiting examples which follow, the parts and percentages indicated are by weight, unless otherwise stated, and the temperatures are in degrees Centigrade.

EXAMPLE 1

Printing of a multicoloured pattern on one side of a woven fabric made of "Tergal" (ethylene terephthalate polymer), weighing 120 g per square meter:

Yellow, red and blue inks are prepared by grinding each of the following dyestuffs very finely and dispersing 6 parts thereof in a solution of 6 parts of ethylcellulose in 88 parts of isopropyl alcohol:

Yellow dyestuff: product resulting from the coupling of barbituric acid with diazotised 2-methoxy-4-nitroaniline.

Red dyestuff: 1-amino-4-hydroxyanthraquinone carrying a benzoyloxyethyl radical bonded in the 2-position via an oxygen atom.

Blue dyestuff: the $\beta$-methoxyethylimide of 1,4-diaminoanthraquinone-2,3-dicarboxylic acid.

Using these inks and several inking rollers, one of the sides of a strip of calendered Kraft paper, weighing 60 g per m$^2$, is printed with engraved cylinders to give a multicoloured pattern, and the printed paper is dried. The auxiliary support thus obtained cannot usefully be applied in the conventional transfer printing process. On the other hand, transfer printing onto a woven fabric made of ethylene terephthalate polymer, under a pressure of 90 mbars, at 210° C. and in the course of 30 seconds, gives a vivid print which has a much greater fastness to resublimation and to light than in the case of the known auxiliary supports.

Instead of the red dyestuff indicated in this example, it is also possible to use 1-amino-2-methoxy-4-(p-toluenesulphonylamino)-anthraquinone, and this gives an auxiliary support with which polyester can be printed, under a pressure of 90 mbars, in shades which are fast to light and to resublimation.

EXAMPLE 2

The procedure of Example 1 is followed, but the blue dyestuff 1-benzoylamino-4-isobutylanilino-anthraquinone and the yellow dyestuff obtained by coupling the naphthanilide of benzoylacetic acid with diazotised nitrotoluidine are used, and the amount of ink used is such that there is 0.6 g of dyestuff per square meter after drying.

The paper thus obtained makes it possible, by heat-transfer, under a pressure of 80 mbars, onto 50/50 polyester/cotton fabric or onto cotton containing 10% of a polyethylene glycol having a molecular weight of 300 to 400, easily to obtain yellow and blue designs when the fabric/paper combination is subjected to a temperature of 220° C.

After the polyethylene glycol has been removed by rinsing with water, these prints are fast to washing (ISO3), to perspiration, to light and to dry cleaning.

EXAMPLE 3

A slightly absorbent paper is printed on a rotary screen, in accordance with the usual technique, using yellow and blue inks containing 10% of the dyestuffs indicated in Example 2, and a red ink containing 10% of the dyestuff obtained by coupling the morpholide of β-hydroxynaphthoic acid with diazotised chloroanisidine, the thickener for the ink being polyvinyl alcohol or carob gum.

The temporary support thus obtained also makes it possible to print cotton fabrics containing 8 to 10% of a polyethylene glycol having a molecular weight of about 400, in shades of remarkable clarity, which are fast to light and to washing.

If the dyestuffs indicated in column I of the table below are used in this example, auxiliary supports are obtained which can be used for printing cotton containing 10% of polyethylene glycol, by transfer at 225° C. and under a pressure of 90 mbars; the shades indicated opposite, in column II, are then obtained, and these shades have a remarkable fastness to wet treatments and to light.

| I | II |
|---|---|
| 1 The γ-(N—ethyl-N—anilino)-propylimide of 1,4-diaminoanthraquinone-2,3-dicarboxylic acid. | blue |
| 2 The phenoxypropylimide of 1,4-diamino-anthraquinone-2,3-dicarboxylic acid. | blue |
| 3 The dyestuff of Example 1 of U.S. Pat. No. 3,766,163. | navy blue |
| 4 A mixture of the above dyestuff (No. 3) and the product resulting from the coupling of the naphthylamide of benzoylacetic acid with diazotised nitrotoluidine. | black |
| 5 1-Benzoylamino-5,8-dixylidinoanthraquinone. | blue |
| 6 1-Benzoylamino-4-(p-butylanilino)-anthraquinone. | blue |
| 7 1,5-Di-(p-butylanilino)-anthraquinone. | violet |
| 8 Brominated 1,5-dixylidinoanthraquinone. | red |
| 9 1,5-Bis-(trifluoromethylanilino)-anthraquinone. | orange-red |
| 10 1,5-Bis-chloroanilino-anthraquinone. | purplish-red |
| 11 1,8-Bis-chloroaniline-anthraquinone. | bluish-red |
| The product resulting from the coupling of the dimethoxyanilide of β-hydroxynaphthoic acid with: | |
| 12 (a) diazotised trifluoromethylaniline, | orange |
| 13 (b) diazotised 5-chloro-2-trifluoromethyl-aniline, | orange |
| 14 (c) diazotised ortho-nitroaniline, | red |
| 15 (d) diazotised ortho-anisidine, | red |
| 16 2-amino-3,4-phthaloylacridone-9. | blue |
| 17 The yellow dyestuff CELLESTREN 5G from BASF. | yellow |
| 18 The violet dyestuff DYBLN R from Du Pont. | violet |
| 19 The blue-green dyestuff DYBLN 2G from Du Pont. | greenish grey-blue |
| The product resulting from the coupling of 1-(phenoxyacetaminophenyl)-3-methyl-5-pyrazolone with: | |
| 20 (a) diazotised nitroaniline, | yellow |
| 21 (b) diazotised nitro-toluidine, | yellow |
| 22 (c) diazotised trifluoromethylaniline, | yellow |
| 23 (d) diazotised aminodiphenyl, | yellow |
| 24 the yellow dyestuff CELLESTREN R from BASF. | golden yellow |

EXAMPLE 4

Yellow, red and blue inks are prepared by dispersing 8 parts of each of the following dyestuffs:

| | |
|---|---|
| (yellow) | 1-(p-phenylbenzoylamino)-anthraquinone, |
| (red) | the phenylamide of 1-phenylazo-2-hydroxy-3-naphthoic acid, and |
| (blue) | amino-phthaloylacridone, | with 6 parts of ethylcellulose in 86 parts of a mixture of isopropyl alcohol and methyl ethyl ketone. Using these inks and several inking rollers, a multicoloured pattern or a single colour is printed on a strip of paper by gravure printing, and the printed paper is then dried.

In order to transfer the pattern from the strip of paper onto a woven or knitted cotton fabric containing polyethylene glycol, the paper is placed in contact with the textile material and the whole is heated at 220° C. under a pressure of 100 mbars.

EXAMPLE 5

An offset ink is prepared in the usual manner by grinding, in linseed oil, the dyestuff obtained by cyclising the product resulting from the condensation of two mols of p-chloroaniline with one mol of chloranil.

Using this ink, a design is printed onto a sheet of paper by offset printing; after drying, the design is transferred, under a pressure of 50 mbars and at 230° C., onto a knitted cotton fabric containing 10% of a polypropylene glycol having an average molecular weight of about 400.

This gives a knitted fabric provided with an orange design which is fast to washing and to light.

EXAMPLE 6

Inks are prepared by dispersing 8 parts of each of the dyestuffs 1, 4, 8 and 24, and 8 parts of a mixture of equal parts of the dyestuffs 17 and 6 in the table following Example 3, with 6 parts of ethylcellulose in 86 parts of a mixture of isopropyl alcohol and methyl ethyl ketone. Using these inks and several inking rollers, a multicoloured pattern or a single colour is printed onto a strip of paper by gravure printing, and the printed paper is then dried.

With the paper thus obtained, a woven cotton fabric, which has been impregnated beforehand, at ambient temperature, with a 15% strength aqueous solution of a polypropylene glycol having a molecular weight of about 425, and has been dried at 105° C., can be printed by heat-transfer, under a pressure of 80 mbars and at a temperature of 230° C., in a contact time of 35 seconds.

After transfer, it is not necessary to rinse the printed fabric in order to remove the polypropylene glycol. The print obtained is fast to washing and to light and it can be subjected to the most varied subsequent treatments (crease-resistant finishes and the like).

A print which is fast to washing and to light is also obtained if a woven 50/50 polyester/cotton fabric is used in this example instead of cotton.

A fast print is also obtained, with the supports in this example, if a woven cotton or polyester/cotton fabric is used which is impregnated with a boric acid ester of the product resulting from the addition of 6 to 8 mols of ethylene oxide onto 1 mol of ethylene glycol or propylene glycol, instead of being impregnated with propylene glycol, in accordance with German Pat. No. 2,524,243.

I claim:

1. Auxiliary supports of cellophane or paper carrying one or more pigments or dyestuffs which contain at least three benzenoid rings and which, at atmospheric pressure, change into the vapour state below 320° C., without substantial decomposition, characterised in that they comprise dyestuffs or pigments which are free from highly ionic groups—and which, at atmospheric pressure and in a transfer time of 35 seconds at 205° C. on cotton containing 8 to 10% of polyethylene glycol, give transfers, the optical density of which is (a) between 0.15 and at most 0.75 when the dyestuffs are present in amounts of 0.6 g to 1.2 g per m$^2$ in the coloured zone of the auxiliary support, and (b) less than half the density obtained with these same dyestuffs under the same transfer conditions, but at 235° C., a temperature at which under 50–120 mbar the said dyestuffs yield transfer prints with an optical density comparable to conventional transfer paper prints at 205° C. under atmospheric pressure.

2. Process for the preparation of new auxiliary supports of cellophane or paper which can be used in dry heat-printing, characterised in that a sheet, strip or tape of cellophane or paper is printed using inks containing one or more pigments or dyestuffs which contain at least three benzenoid rings, which are free from highly ionic groups and change into the vapour state below 320° C., without substantial decomposition, so as to give a uniform layer of a single colour or a design of one or more colours, in which said dyestuffs or pigments, in a transfer time of 35 seconds, at atmospheric pressure and at 205° C., do not reach 60%, of the intensity obtained with these same dyestuffs by transfer at 235° C., and give transfers, the optical density of which is (a) between 0.15 and at most 0.75 when the dyestuffs are present in amounts of 0.6 to 1.2 g per m$^2$ in the coloured zone of the auxiliary support and (b) less than half of the density obtained with these same dyestuffs under the same transfer condition but at 235° C., a temperature at which under 50–120 mbar the said dyestuffs yield transfer prints with an optical density comparable to conventional transfer paper prints at 205° C. under atmospheric pressure.

3. Auxiliary supports according to claim 1, characterised in that they comprise a flexible inert base, made of cellophane or paper, in the form of a sheet, tape or strip, of which at least one of the sides carries, in the form of a plain coloured layer or a design, one or more said dyestuffs which vaporise or sublime below 270° C., without substantial decomposition, and which, at atmospheric pressure, reach the maximum of their transfer curves above 230° C.

4. Supports according to claim 2, characterised in that the inert base consists of a sheet or strip of paper, and in that the dyestuffs contain, bonded to a monoanthraquinone nucleus, a phenyloxyacetamino, phenyl—OCO—O—, phenyl—O—CO—NH— or benzoylamino group, in which the phenyl or benzoyl radical can carry one or more substituents chosen from the group comprising methyl, ethyl, methoxy, ethoxy and trifluoromethyl radicals and fluorine, chlorine or bromine atoms.

5. Supports according to claim 1 or 3, characterised in that they comprise at least one monoazo or disazo dyestuff having a phenoxyacetamino group in which the phenyl radical which is unsubstituted or carries an alkyl or alkoxy radical having 1 to 4 carbon atoms.

6. Paper supports according to claim 3, characterised in that they carry one or more dyestuffs from the group comprising:
   (a) halogenated dianilinoanthraquinones,
   (b) N-alkylimides of 1,4-diaminoanthraquinone-2,3-dicarboxylic acid, in which the alkyl carries one or two benzene radicals,
   (c) arylides of 1-phenylazo-2-hydroxy-3-naphthoic acid,
   (d) naphthylamides of α-phenylazo-acetylacetic acids and phenylamides of α-phenylazo-benzoylacetic acids, and
   (e) 1-benzoylamino-anthraquinones which carry a phenyl—NH— radical in the 4-, 5- or 8-position and in which the phenyl and benzoyl radicals can carry methyl, ethyl, methoxy, ethoxy or trifluoromethyl substituents or a fluorine, chlorine or bromine atom.

7. Supports according to claim 6, characterised in that they carry at least one monoazo dyestuff of which the coupler is an arylide of β-hydroxynaphthoic acid or a naphthanilide of acetylacetic acid or benzoylacetic acid, and which does not have a nitrogen-containing substituent.

8. Supports according to claim 6, characterised in that they comprise a coloured design which essentially consists of a binder which is stable at 200° C. and at least one 1-benzoylamino-4- or -5-anilinoanthraquinone in which at least one of the benzoyl and anilino radicals carries one or more of the following substituents: fluorine, chlorine, low molecular weight alkyl or alkoxy, trifluoromethyl or bromine.

9. Supports according to claim 1, characterised in that they comprise a sheet of paper carrying at least 0.1 to 1.0 gram of dyestuff per square meter.

10. Process for the dry heat-printing of synthetic or natural materials, characterised in that the printed surface of an auxiliary support according to any one of claims 3, 4-7, 8-9 and 1 is brought into contact with the material of which all or part is to be dyed or heat-printed, and in that the whole is heated at 190°–230° C. under a pressure of 50 to 100 mbars.

11. Process according to claim 10, characterised in that polyacrylonitrile or polyamide is printed.

12. Process according to claim 10, characterised in that cotton or blends of cotton and polyester, which contain a cotton swelling agent, are printed.

13. Process according to claim 12, characterised in that, after dry printing, the cotton swelling agent is removed from the fibre, preferably by steam distillation or by rinsing.

14. Processing according to any one of claims 10 to 13, characterised in that the transfer is carried out under a contact pressure of the print-back cloth on the textile materials to be transfer printed of at least 15 g/cm$^2$, preferably at least 20 g/m$^2$.

15. Organic or aqueous inks for the printing of transfer papers, characterised in that they contain 5 to 15% of at least one of the dyestuffs defined in any one of claims 3, 4-7, 8 and 1.

* * * * *